US00PP16942P2

(12) United States Plant Patent
Gossett

(10) Patent No.: US PP16,942 P2
(45) Date of Patent: Aug. 8, 2006

(54) ***HEUCHERA* PLANT NAMED 'TNHEU044'**

(50) Latin Name: *Heuchera hybrida*
Varietal Denomination: TNHEU044

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 103 days.

(21) Appl. No.: 11/089,624

(22) Filed: Mar. 23, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman LLP

(57) ABSTRACT

A new and distinct *Heuchera* plant characterized by large, very shiny, purple black colored leaves, a vigorous, mounding habit.

1 Drawing Sheet

Botanical denomination *Heuchera hybrida.*
Variety designation: 'TNHEU044'.

The present invention relates to a new and distinct cultivar of *Heuchera hybrida* and given the cultivar name of 'TNHEU044'. *Heuchera* is in the family Saxifragaceae. *Heuchera* 'TNHEU044' originated from a cross between unknown parents. This new *Heuchera* was selected from seedlings grown from select, experimental and unnamed, interspecific hybrids that were open pollinated in the field in Canby, Oreg. Given its floral characteristics and the silvering and red on the leaves, it is probable that *Heuchera americana* is in its parentage.

This new *Heuchera* is distinguished by:

1. Large, very shiny, purple black colored leaves.
2. Excellent winter color.
3. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows *Heuchera* 'TNHEU044' growing in the soil in the ground in the trial beds in spring in Canby, Oreg.

DETAILED PLANT DESCRIPTION

The following is a detailed description of the new *Heuchera* cultivar based on observations of a one-year-old specimen grown in the ground in full sun under typical outdoor conditions in the trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:
- *Form.*—Basal rosette, herbaceous perennial.
- *Hardiness.*—USDA Zone 4 to 9.
- *Size.*—35 cm tall from the ground to the top of the foliage and 60 cm wide.
- *Habit.*—Rounded.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Orbicular to slightly ovate.
- *Lobing/division.*—5 shallow rounded lobes, with 1 to 2 shallow secondary lobes.
- *Veration.*—Palmate.
- *Margins.*—Crenate.
- *Apex.*—Obtuse.
- *Base.*—Cordate, lobes overlapping.
- *Blade size.*—13 cm long and 13 cm wide.
- *Surface texture.*—Sparsely puberulous on abaxial side, glabrous adaxial.
- *Petiole description.*—34 cm. long and 2 mm wide, sparsely glandular puberulent, Red Purple 59A.
- *Leaf color.*—Summer adaxial — Between Greyed Purple 187A and Brown 200A. Spring adaxial — Same with a light veil white making it closest to Greyed-Purple 187B. Summer and spring abaxials — Between Red Purple 71A and Red Purple 59A.

Inflorescence:
- *Type.*—Thyrse.
- *Number of flowers.*—200 to 250 per thyrse.
- *Number of thyrse.*—14.
- *Peduncle.*—85 to 122 cm tall and 6 mm wide near the base, very dark in color, Brown 200A to Red Purple 59A, glandular puberulent, with 2 to 4 cauline leaves (ovate, 4 to 7 cm long and 4 to 7 cm wide).

*Pedicel*.—2 to 5 mm long, glandular puberulent, closest in color to Greyed Purple 187A, but darker.

*Bloom period*.—June through July in Canby, Oreg.

Flower bud:

*Size*.—2 mm wide and 3 mm long.

*Description*.—Glandular puberulent, ovoid.

*Color*.—Greyed Purple 187A.

Flower:

*Type*.—Perfect, zygomorphic.

*Shape*.—Insignificant, campanulate.

*Size*.—7 mm long and 4 mm wide, including extruding pistil.

*Petal description*.—5, inconspicuous, 3 mm long, White 155D on both sides, spatulate with a clawed base, apex acute, margin entire.

*Calyx description*.—4 mm deep and wide, with 5 lobes, each divided ⅓ way to the base, with glandular hairs, urceolate, red brown in color on both sides, Greyed Orange 175A with yellow green lobes, Yellow Green 148A.

*Stamen description*.—5.

*Pistil description*.—7 mm long, Yellow Green 152D overall.

*Pollen color*.—No pollen, male sterile.

*Fragrance*.—None.

*Lastingness*.—Each thyrse blooms for about 2 weeks on the plant.

Fruit:

*Type*.—Two-beaked ovoid capsule.

*Fertility*.—Low.

*Color*.—Tan. Grey-Brown 199C.

Seed:

*Shape*.—Linear.

*Size*.—2 mm. long.

*Color*.—Black. RHS 202A.

Disease and pest tolerance: Excellent disease resistance to powdery mildew, the common problem of *Heuchera*. Susceptible to root weevils like all *Heuchera*.

COMPARISON TO SIMILAR *HEUCHERAS*

Compared to *Heuchera* 'Black Beauty' (U.S. Plant Pat. No. 13,288), *Heuchera* 'TNHEU044' has leaves that are larger, darker, rounder with margins that do not undulate.

Compared to *Heuchera* 'Obsidian' (U.S. Plant Pat. No. 14,836), this new cultivar has a much larger habit and larger, shinier leaves.

I claim:

1. A new and distinct *Heuchera* plant as herein illustrated and described.

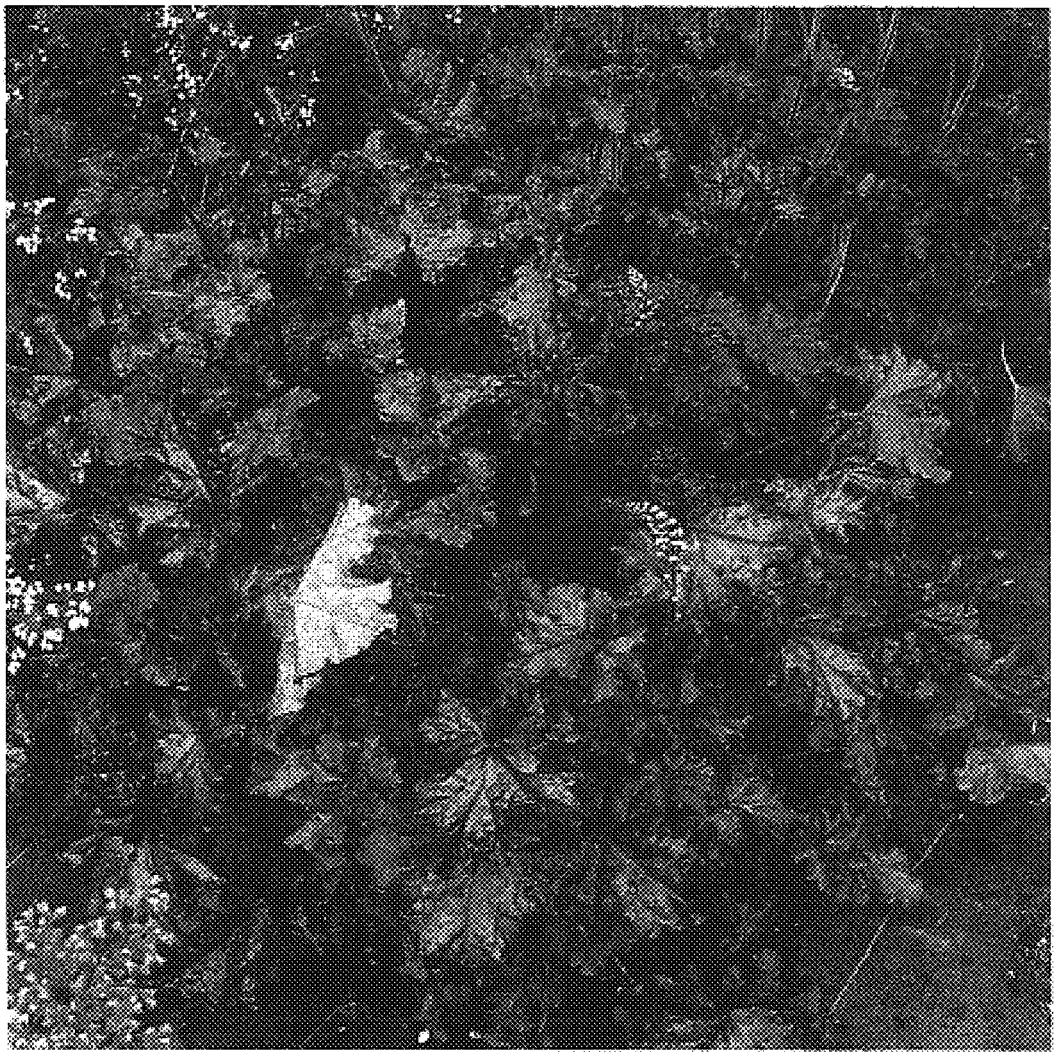

* * * * *